US012747508B2

(12) United States Patent
Buckley et al.

(10) Patent No.: US 12,747,508 B2
(45) Date of Patent: Sep. 29, 2026

(54) ELECTROCHEMICAL TRANSFORMATIONS

(71) Applicant: Loughborough University, Loughborough (GB)

(72) Inventors: Benjamin Roger Buckley, Loughborough (GB); Jin Xuan, Loughborough (GB); Anas Alkayal, Loughborough (GB); Faraz Montazersadgh, Loughborough (GB)

(73) Assignee: Loughborough University, Loughborough (GB)

( * ) Notice: Subject to any disclaimer, the term of this patent is extended or adjusted under 35 U.S.C. 154(b) by 0 days.

(21) Appl. No.: 18/291,967

(22) PCT Filed: Jul. 26, 2022

(86) PCT No.: PCT/GB2022/051952
§ 371 (c)(1),
(2) Date: Jan. 25, 2024

(87) PCT Pub. No.: WO2023/007144
PCT Pub. Date: Feb. 2, 2023

(65) Prior Publication Data

US 2024/0376612 A1 Nov. 14, 2024

(30) Foreign Application Priority Data

Jul. 26, 2021 (GB) ..................................... 2110687

(51) Int. Cl.

| | |
|---|---|
| ***C25B 3/05*** | (2021.01) |
| ***C07D 317/20*** | (2006.01) |
| ***C25B 3/07*** | (2021.01) |
| ***C25B 3/23*** | (2021.01) |
| ***C25B 3/25*** | (2021.01) |
| ***C25B 11/057*** | (2021.01) |

(52) U.S. Cl.
CPC .............. *C25B 3/07* (2021.01); *C07D 317/20* (2013.01); *C25B 11/057* (2021.01)

(58) Field of Classification Search
CPC ................ C25B 3/05; C25B 3/23; C25B 3/25
USPC ......................................... 205/422, 423, 427
See application file for complete search history.

(56) References Cited

U.S. PATENT DOCUMENTS

2019/0055656 A1* 2/2019 Kenis ......................... C25B 3/25
2020/0399489 A1* 12/2020 Koganehira ......... C09D 11/037

OTHER PUBLICATIONS

Hunsom et al., "Product Distribution of Electrochemical Conversion of Glycerol via Pt Electrode: Effect of Initial pH," International Journal of Electrochemical Science (Sep. 1, 2013), vol. 8, No. 9, pp. 11288-11300. (Year: 2013).*

Nanda et al., "Catalytic Conversion of Glycerol for Sustainable Production of Solketal as a Fuel Additive: A Review," Renewable and Sustainable Energy Reviews (Apr. 1, 2016), vol. 56, pp. 1022-1031. (Year: 2016).*

(Continued)

*Primary Examiner* — Edna Wong
(74) *Attorney, Agent, or Firm* — HOVEY WILLIAMS LLP

(57) ABSTRACT

A process for synthesising a defined compound, such as solketal, wherein the process comprises subjecting a solution comprising another defined compound, such as glycerol, to a potential difference. A compound and a composition obtainable by the process, and a product comprising the compound or the composition.

13 Claims, 3 Drawing Sheets

(56) References Cited

OTHER PUBLICATIONS

International Search Report and Written Opinion mailed Jan. 25, 2023 in corresponding PCT/GB2022/051952, 17 pages.
Hunsom et al., "Product Distribution of Electrochemical Conversion of Glycerol via Pt Electrode: Effect of Initial pH," International Journal of Electrochemical Science, vol. 8, No. 9, Jan. 1, 2013 (Jan. 1, 2013), pp. 11288-11300, XP055956909, Serbia, ISSN: 1452-3981, 13 pages.
Fructuoso et al., "Indirect, anodic oxidation of D-glucitol in aqueous calcium iodide," Carbohydrate Research, vol. 105, No. 1, Jan. 1, 1982 (Jan. 1, 1982), pp. 158-164, XP085399472, ISSN: 0008-6215, DOI: 10.1016/S0008-6215(00)81862-5, 7 pages.

* cited by examiner

ELECTROCHEMICAL TRANSFORMATIONS

RELATED APPLICATIONS

This application is a U.S. National Stage of the International Patent Application No. PCT/GB2022/051952, filed Jul. 26, 2022, which is hereby incorporated by reference in its entirety, and which claims priority to Great Britain Patent Application No. 2110687.7, filed Jul. 26, 2021, which is also hereby incorporated by reference in its entirety.

FIELD OF THE INVENTION

The present invention relates to a process for the synthesis of compounds of Formula (I), such as solketal. Such compounds can be used as a solvent, a fuel additive, a pharmaceutical intermediate, and/or in applications such as air care, fragrances, paints and varnishes, printing inks, household and institutional cleaners, and/or leather treatments. The present invention also relates to compounds of Formula (I) obtainable by the process, products containing such compounds, uses of such compounds, and compositions comprising such compounds.

BACKGROUND

There is an industry-wide desire to move away from traditional fossil fuel-based products. New technologies that switch away from a fossil fuel-based economy are of significant value. For example, the market value of biofuels is projected to be USD 154 billion by 2024.

A few specific product lines exist as replacements for fossil fuel-based products. For example, BASF recently switched to biomass feedstocks for some products (e.g. Styropor®).

Solketal is another bio-based replacement for fossil fuel-based chemicals and is marketed by Solvay under the brand name Augeo®.

Solketal is conventionally synthesised from the condensation of glycerol and acetone. Owing to this, solketal can be made from non-animal-based materials and has a low carbon footprint. Glycerol is a waste product from factories and therefore its use in the synthesis of solketal can be considered to be environmentally benign.

Solketal can be used as an organic solvent, a fuel additive, a pharmaceutical intermediate, and in applications such as air care, fragrances, paints and varnishes, printing inks, household and institutional cleaners, and leather treatments. The global market for solketal is projected to reach USD 14 million by 2026. Solketal also has the benefit that it is not toxic to humans or the environment.

SUMMARY OF THE INVENTION

According to a first aspect, the present invention provides a process for synthesising a compound according to Formula (I):

Formula (I)

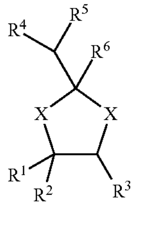

the process comprises subjecting a solution comprising a compound according to Formula (II):

Formula (II)

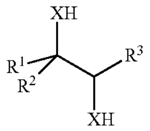

to a potential difference. For the compounds according to Formulae (I) and (II), each X is independently selected from the group consisting of O, S, $NR^Y$ and $PR^Y$. Each of $R^1$ to $R^6$ and $R^Y$ is a group selected from the list consisting of hydrogen, $C_1$-$C_{12}$ alkyl, $C_2$-$C_{12}$ alkenyl, $C_2$-$C_{12}$ alkynyl, $C_6$-$C_{12}$ aryl, and $C_3$-$C_{12}$ heterocyclyl. Each of $R^1$ to $R^6$ and $R^Y$ optionally contains one or more heteroatom containing groups. Formulae (I) and (II) include tautomeric and stereochemically isomeric forms thereof.

Preferably the compound according to Formula (I) is solketal (CAS 100-79-8, (2,2-dimethyl-1,3-dioxolan-4-yl) methanol):

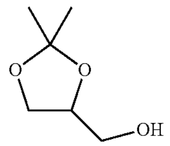

Solketal

As discussed above, solketal finds applications in a variety of fields, usually as a solvent. Thus, processes to synthesise compounds of Formula (I), such as solketal, are particularly desirable.

The present inventors have surprisingly determined that compounds according to Formula (I), such as solketal, can be synthesised using the process of the first aspect.

A key difference between the process of the first aspect and conventional processes is that conventional processes do not apply a potential difference to compounds of Formula (II) such as glycerol to prepare compounds of Formula (I). In other words, the process of the first aspect is an electrochemical process, unlike conventional processes. However, the present inventors have determined that applying the potential difference is necessary for the reaction to take place under the process of the first aspect.

The process of the first aspect also provides a number of significant and surprising advantages over conventional processes.

Conventional processes for the manufacture of solketal have drawbacks. For example, they typically react glycerol with acetone in the presence of a strong acid and/or a heterogeneous catalyst, at high temperatures (>100° C.), using $CO_2$ at high pressures (>5000 kPa), and require the distillation of the excess reagent ketone, acetone, from the desired solketal product. These parameters mean that conventional processes for the manufacture of solketal encounter issues with safety, are inefficient, are complex, and utilize a large amount of energy, causing a high carbon footprint.

Therefore, new processes for the synthesis of solketal and similar compounds are desirable.

Processes to synthesise compounds, such as solketal, that can avoid strong acids, heterogeneous catalysts, high temperatures, high pressures and/or the distillation of excess reagents are also desirable.

As evidenced by the examples, the process can operate efficiently without either strong acids or heterogeneous catalysts. Therefore, the process has increased safety and can operate without having to separate catalysts or by-products from the synthesised compound of Formula (I), making the process more straightforward and efficient.

As also evidenced by the examples, the process can operate efficiently at room temperature and standard atmospheric pressures. Therefore, high temperatures (>100° C.) or high pressures (>5000 kPa) used in conventional processes for the synthesis of compounds such as solketal are not necessary under the process of the present invention. This reduces the energy consumption and carbon footprint of the process and increases the safety of the process.

As also evidenced by the examples, the process does not require the addition of a ketone, such as acetone, to form the desired compound of Formula (I). Acetone is a further raw ingredient that is be required by conventional processes, making those process more complex, and conventional processes typically need to remove the excess ketone from the desired product by distillation, which requires significant amounts of energy.

In one embodiment the potential difference is provided from a renewable energy source, such as solar, wind or hydroelectric energy. This further reduces the carbon footprint of the process.

The process of the present invention can therefore overcome several significant drawbacks of conventional processes. In particular, the process of the present invention can be safer, can be more straightforward, can be more efficient, can consume less energy, and can have a lower carbon footprint than conventional processes for preparing compounds of Formula (I), such as solketal.

In one embodiment the solution is contacted with carbon dioxide. This provides a use for carbon dioxide, which is a fossil fuel by-product. The usage and storage of carbon dioxide is estimated to contribute GBP 5-9 bn to the UK economy by 2030 and 30 bn by 2050. Without being bound by theory it is thought that the carbon dioxide can dissolve into the solution to provide carbonate ions, which may assist the process.

The process synthesises the compound of Formula (I) from a compound according to Formula (II). Preferably the compound according to Formula (II) is glycerol (CAS 56-81-5, also known as glycerine or propane-1,2,3-triol):

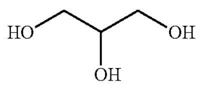

Glycerol

Glycerol is particularly preferred as it is a by-product of biodiesel production. Using such glycerol as the compound of Formula (II) can therefore make use of this waste by-product.

The generation of traces of compounds of Formula (I), such as solketal, has been described previously.

For example, Int. J. Electrochem. Sci., 8 (2013) 11288-11300 describes traces of solketal being generated. This was performed at a low pH (i.e. not including a Brønsted base), without the solution being contacted with $CO_2$, and using cylindrical Pt grids as the electrodes. Solketal was formed as part of a complex mixture of other compounds, and the document focusses on the synthesis of a selection of other compounds. Solketal was not reported as being prepared in any significant yield.

Carbohydrate Research, 105 (1982) 158-64 describes processes for the electrochemical oxidation of the sugar D-glucitol. This was performed without any Brønsted base, without the solution being contacted with $CO_2$, and using Pt electrodes. There is no mention of glycerol being used as the compound of Formula (II) or solketal being produced as the compound of Formula (I). Any compounds of Formula (I) are not reported as being prepared in any significant yield. Installation of the acetal (isopropylidene) group is carried out following the electrochemical process using classical chemical techniques, requiring the addition of acetone, with the sole purpose of identifying products made by GC-MS (Gas Chromatography—Mass Spectrometry). There is no suggestion that the acetal group could be installed without adding acetone.

The process of the first aspect provides a compound according to Formula (I), such as solketal. According to a second aspect, the present invention provides a compound according to Formula (I), wherein the compound is obtainable by (e.g. obtained by) the method of the first aspect.

The compound of Formula (I) may be contained in a composition. Thus, according to a third aspect, the present invention provides a composition comprising a compound of Formula (I). The composition is obtainable by (e.g. obtained by) the method of the first aspect and/or comprises a by-product characteristic of the method of the first process, such as a compound having the molecular formula $C_7H_{12}O_2$ (e.g. ethyl cyclopentanolone) and/or formic acid.

The compounds of Formula (I) obtainable by (e.g. obtained by) the process of the first aspect, and compositions thereof find application in a variety of fields and can be used as or incorporated into a variety of products. Thus, according to a fourth aspect the claimed invention provides a product comprising a compound according to the second aspect or a composition of the third aspect, wherein the product is:

a) a solvent;
b) a fuel, for example a liquid petroleum fuel, such as gasoline (petrol), diesel and/or kerosene;
c) a pharmaceutical intermediate;
d) a pharmaceutical carrier;
e) an air care product, for example a fragrance diluent, base or carrier, such as for an air freshener (e.g. a plug-in air freshener, a diffuser, or a spray) or a candle;
f) a paint or varnish, such as an epoxy resin, for example for application to automobiles, metal and/or wood;
g) an ink, such as a printing ink;
h) a cleaning agent, such as a household or institutional cleaning agent, for example a surface cleaning agent and/or a degreaser; and/or
i) a leather treatment agent, for example a penetrating agent, an adhesion promoter, a dye diluter, and/or a lacquer for paint.

Thus, according to a fifth aspect the claimed invention provides a use of a compound according to the second aspect or a composition according to the third aspect in or as:

a) a solvent;
b) a fuel additive, as an additive for a liquid petroleum fuel, such as gasoline (petrol), diesel and/or kerosene;
c) a pharmaceutical intermediate;
d) a pharmaceutical carrier;
e) an air care product, for example a fragrance diluent, base or carrier, such as for an air freshener (e.g. a plug-in air freshener, a diffuser, or a spray) or a candle;

f) a paint or varnish, such as an epoxy resin, for example a paint or varnish for application to automobiles, metal and/or wood;

g) an ink, such as a printing ink;

h) a cleaning agent, such as a household or institutional cleaning agent, for example a surface cleaning agent and/or a degreaser; and/or i) a leather treatment agent, for example a penetrating agent, adhesion promoter, dye diluter, and/or lacquer for paint.

DETAILED DESCRIPTION

Compounds of Formula (I)

The first aspect defines a process for synthesising a compound according to Formula (I):

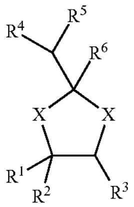

Formula (I) includes tautomeric and stereochemically isomeric forms thereof.

Each X is independently selected from the list consisting of O, S, $NR^Y$ and $PR^Y$. The X groups may be the different, but preferably they are the same. Each X group may be selected from the list consisting of O, $NR^Y$ and S, preferably the group consisting of O and $NR^Y$. Preferably both X groups are selected from the list consisting of O, $NR^Y$ and S, preferably the list consisting of O and $NR^Y$. Preferably at least one X is O. Preferably both X groups are O, such that the compound of Formula (I) can be termed an acetal. N and O are more preferable, and O is most preferable, because of a reduced susceptibility to oxidation compared to S and P.

Each of $R^1$ to $R^6$ and $R^Y$ is a group selected from the list consisting of hydrogen, $C_1$-$C_{12}$ alkyl, $C_2$-$C_{12}$ alkenyl, $C_2$-$C_{12}$ alkynyl, $C_6$-$C_{12}$ aryl and $C_3$-$C_{12}$ heterocyclyl.

The prefix "$C_{x-y}$" (where x and y are integers) as used herein refers to the number of carbon atoms in a given group. For example, a $C_{1-6}$ alkyl group contains from 1 to 6 carbon atoms, and a $C_{3-6}$ alkyl group contains from 3 to 6 carbon atoms.

The term "alkyl" may refer to a linear, branched and/or cyclic ("cycloalkyl") hydrocarbon group that is saturated. Examples of alkyl groups include methyl, ethyl, n-propyl, isopropyl, n-butyl, isobutyl, sec-butyl, tert-butyl, n-pentyl, isopentyl, neopentyl or hexyl and the like. The term "cycloalkyl" refers to cyclic hydrocarbon groups. Examples of cycloalkyl groups include cyclopropyl, cyclobutyl, cyclopentyl, or cyclohexyl.

The term "alkenyl" may refer to a linear, cyclic ("cycloalkenyl") and/or branched hydrocarbon group containing one or more carbon-carbon double bond. Examples of such groups include vinyl, allyl, prenyl, isoprenyl.

The term 'alkynyl' may refer to a linear, cyclic and/or branched hydrocarbon group containing one or more carbon-carbon triple bond.

The term "aryl" as used herein refers to carbocyclic aromatic groups including phenyl, benzyl, naphthyl, anthracenyl, pyrenyl, chrysenyl, benz[a]anthracenyl, fluoranthene, indenyl, and tetrahydronaphthyl groups.

The term "heterocyclyl" shall, unless the context indicates otherwise, include both aromatic (i.e. heteroaryl) and non-aromatic (i.e. heterocycloalkyl/heterocycloalkenyl) ring systems. Thus, for example, the term "heterocyclyl group" includes within its scope aromatic, non-aromatic, unsaturated, partially saturated and fully saturated heterocyclyl ring systems. Heterocyclyl groups may include heteroatoms selected from the list consisting of oxygen, nitrogen and sulfur. In general, unless the context indicates otherwise, such groups may be monocyclic or bicyclic and may contain, for example, 4 to 10 ring members, more usually 5 to 10 ring members.

Examples of monocyclic groups are groups containing 4, 5, 6, 7 and 8 ring members, more usually 4 to 7, and preferably 5, 6 or 7 ring members, more preferably 5 or 6 ring members. Examples of bicyclic groups are those containing 8, 9 and 10 ring members. Non-aromatic heterocyclic groups may include oxiranes, aziridines, axetidines, oxetanes, dihydrofurans, tetrahydrofurans, pyrrolidines, piperidines, piperazines, dioxanes, decahydroisoquinolines and morpholines.

The heterocyclyl groups can be heteroaryl groups having from 5 to 10 ring members. The term "heteroaryl" is used herein to denote an aromatic heterocyclyl group. The The term "heteroaryl" embraces polycyclic (e.g. bicyclic) ring systems wherein one or more rings are non-aromatic, provided that at least one ring is aromatic. In such polycyclic systems, the group may be attached by an aromatic ring, or by a non-aromatic ring. Examples of such polycyclic systems include 1,4,5,6-tetrahydrocyclopenta[b]pyrrole, indoline, tetrahydroquinoline, tetrahydroisoquinoline, 1,2-dihydroquinoline, 1,2-dihydroisoquinoline, 2H-benzo[e][1,3] oxazine, 2H-benzo[b][1,4]-oxazine, 2H-benzo[e][1,2] oxazine, 1H-isochromene and 2H-chromene. The heteroaryl group may be a five membered or six membered monocyclic ring or a bicyclic structure formed from fused five and six membered rings or two fused six membered rings. Each ring may contain up to five heteroatoms typically selected from nitrogen, sulphur and oxygen. The heteroaryl group may contain one or two or more ring nitrogen atoms. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. Examples of heteroaryl groups include pyrrole, furan, thiophene, imidazole, furazan, oxazole, oxadiazole, oxatriazole, isoxazole, thiazole, thiadiazole, isothiazole, pyrazole, triazole, tetrazole, pyridine, pyrazine, pyridazine, pyrimidine, triazine, 1H-indole, 2H-isoindole, benzimidazole, 4-azaindole, 5-azaindole, 6-azaindole, 7-azaindole, benzofuran, isobenzofuran, benzo[c]thiophene, benzo[b]thiophene, benzo[d]isoxazole, benzo[d]thiazole, quinolone, isoquinoline, quinoxaline, phthalazine, quinazoline, cinnoline and 1,8-naphthyridine.

It will be understood that the alkyl, alkenyl, alkynyl, aryl and heterocyclyl groups are not mutually exclusive and can be intermixed between these groups within the claim scope, for example to form a group containing an alkyl and an aryl group. However, the overall limit of the number of carbons should be adhered to, for example where an aryl group is present there must be from 6 to 12 carbon atoms present in that overall R group, including any alkyl moieties.

Each of $R^1$ to $R^6$ and $R^Y$ may be a group selected from the list consisting of hydrogen, $C_1$-$C_8$ alkyl, $C_2$-$C_8$ alkenyl, $C_2$-$C_8$ alkynyl, $C_6$-$C_8$ aryl, and $C_4$-$C_8$ heterocyclyl. Each of $R^1$ to $R^6$ and $R^Y$ may be a group selected from the list consisting of hydrogen and $C_1$-$C_8$ alkyl. Preferably each of $R^1$ to $R^6$ and $R^Y$ may be a group selected from the list consisting of hydrogen and $C_1$-$C_4$ alkyl; such as hydrogen, $C_1$ alkyl and $C_2$ alkyl. Each of $R^1$ to $R^6$ and $R^Y$ may be limited to such groups independently of the other R groups.

Preferably $R^1$ is hydrogen. Preferably $R^2$ is hydrogen. Preferably $R^3$ is —$CH_2OH$. Preferably $R^4$ is hydrogen. Preferably $R^5$ is hydrogen. Preferably $R^6$ is methyl. Where $R^6$ is a hydrocarbon group (e.g. $C_1$-$C_{12}$ alkyl, $C_2$-$C_{12}$ alkenyl, $C_2$-$C_{12}$ alkynyl, $C_6$-$C_{12}$ aryl, or $C_4$-$C_{12}$ heterocyclyl group, such as a methyl group) the compound of Formula (I) can be termed a ketal, which is preferable.

In one embodiment the compound of Formula (I) has 80 carbon atoms or fewer, such as 60 carbon atoms or fewer, or 40 carbon atoms or fewer, preferably 30 carbon atoms or fewer, such as 20 carbon atoms or fewer, for example 10 carbon atoms or fewer, more preferably 8 carbon atoms or fewer. For example, the compound of Formula (I) may have from 4 to 80 carbon atoms, or from 4 to 60 carbon atoms, such as from 5 to 20 carbon atoms, or from 6 to 8 carbon atoms.

Each of $R^1$ to $R^6$ and $R^Y$ optionally contains one or more, such as one, two or three, heteroatom containing groups. Preferably each of $R^1$ to $R^6$ and $R^Y$ contains 0 or 1 heteroatom containing group. The optional heteroatom containing groups may be independently selected from the list consisting of cyano, halogen, boronic acid, boronate ester, ether, alcohol (i.e. hydroxyl), carbonyl, ester, carboxylic acid, amine, amide, urea, carbamate, sulfonate ester, sulfonamide, sulfone and sulfoxide. For example, the optional heteroatom containing groups may be independently selected from the list consisting of cyano, halogen, ether, alcohol, carbonyl, ester, carboxylic acid, amine, amide, urea and carbamate. Halogen may be selected from F, Cl, Br and I, for example F, Cl and Br, or preferably F and Cl. In particular, each $R^Y$ may be a protecting group for the N or P atom to which it is attached. The most preferable heteroatom containing group for $R^1$ to $R^6$ is alcohols. Preferably $R^3$ contains one heteroatom containing group, such as an alcohol. Preferably each of $R^1$, $R^2$, $R^4$, $R^5$ and $R^6$ are, independently, unsubstituted, i.e. contain 0 heteroatom containing groups.

The compound according to Formula (I) may be defined by Formula (Ia):

Formula (Ia)

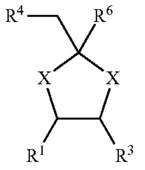

wherein:

- each X is independently selected from N and O; preferably both X groups are O,
- $R^1$, $R^3$, $R^4$ and $R^6$ may each independently be a group selected from the list consisting of hydrogen, $C_1$-$C_{12}$ alkyl, $C_2$-$C_{12}$ alkenyl, $C_2$-$C_{12}$ alkynyl, $C_6$-$C_{12}$ aryl, and $C_3$-$C_{12}$ heterocyclyl; preferably $R^1$, $R^3$, $R^4$ and $R^6$ are each independently a group selected from the list consisting of hydrogen, $C_1$-$C_8$ alkyl, $C_2$-$C_8$ alkenyl, $C_2$-$C_8$ alkynyl, $C_6$-$C_8$ aryl, and $C_3$-$C_8$ heterocyclyl, and
- $R^1$, $R^3$, $R^4$ and $R^6$ may each independently contain one or more heteroatom containing groups; preferably one or two heteroatom groups, for example wherein the heteroatom groups are alcohol groups.

The compound according to Formula (I) may be defined by Formula (Ib):

Formula (Ib)

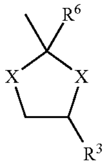

wherein:

- each X is independently selected from N and O; preferably both X groups are O,
- $R^3$ and $R^6$ may each independently be a group selected from the list consisting of hydrogen, $C_1$-$C_{12}$ alkyl, $C_2$-$C_{12}$ alkenyl, $C_2$-$C_{12}$ alkynyl, $C_6$-$C_{12}$ aryl, and $C_3$-$C_{12}$ heterocyclyl; preferably $R^3$ and $R^6$ are each independently a group selected from the list consisting of hydrogen, $C_1$-$C_8$ alkyl, $C_2$-$C_8$ alkenyl, $C_2$-$C_8$ alkynyl, $C_6$-$C_8$ aryl, and $C_3$-$C_8$ heterocyclyl, and
- $R^3$ and $R^6$ may each independently contain one or more heteroatom containing groups; preferably one or two heteroatom groups, for example wherein the heteroatom groups are alcohol groups.

It will be understood that the definitions of optional and preferable groups described in relation to Formula (I) apply equally to Formulae (Ia) and (Ib) unless they are contradictory.

Most preferably the compound according to Formula (I) is solketal:

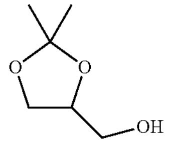

Solketal

Solketal corresponds to Formula (I) wherein both X groups are O, $R^1$ is hydrogen, $R^2$ is hydrogen, $R^3$ is —$CH_2OH$, $R^4$ is hydrogen, $R^5$ is hydrogen, and $R^6$ is methyl.

The purity of the solketal produced by this method may be 20% or more, such as 40% or more, or 45% or more, preferably 50% or more, or 60% or more by moles, relative to glycerol. The purity may be 90% or lower, such as 80% or lower, or 75% or lower, such as 70% or lower. The purity may be from 20% to 90%, such as from 40% to 80%, or from 50% to 75%. A reaction product of the claimed process may include solketal in such a yield. In other words, the solketal produced by this electrochemical method may be purer than has previously been achieved by electrochemical means, for example due to fewer and/or a lower amount of by-products being produced.

Compounds of Formula (II)

The process synthesises the compound according to Formula (I) from a compound according to Formula (II):

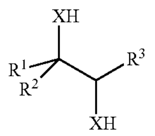

Formula (II) includes tautomeric and stereochemically isomeric forms thereof.

The options described above for the X, $R^1$ to $R^3$ and $R^Y$ groups of Formula (I) apply equally to the groups in Formula (II) with the same designation (e.g. $R^1$ of Formula (I) corresponds with $R^1$ of Formula (II)).

In one embodiment the compound of Formula (II) has 40 carbon atoms or fewer, such as 30 carbon atoms or fewer, or 20 carbon atoms or fewer, preferably 15 carbon atoms or fewer, such as 10 carbon atoms or fewer, for example 7 carbon atoms or fewer, more preferably 5 carbon atoms or fewer. For example, the compound of Formula (II) may have from 2 to 40 carbon atoms, or from 2 to 20 carbon atoms, such as from 3 to 10 carbon atoms, or from 3 to 5 carbon atoms.

Examples of compounds of Formula (II) include glycerol, ethylene glycol, 1,2-propane diol, and amino alcohols such as glycinol. Most preferably the compound according to Formula (II) is glycerol (also known as glycerine):

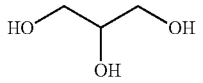

Glycerol

Glycerol corresponds to Formula (II) wherein both X groups are O, $R^1$ is hydrogen, $R^2$ is hydrogen, and $R^3$ is $-CH_2OH$.

Glycerol is particularly preferred as it is a by-product of biodiesel production. Crude glycerol can be obtained from such processes at 40-90 wt % purity. Using such glycerol can make use of this waste by-product.

The compound according to Formula (II) may initially (i.e. before the potential difference is applied) be present in the solution at a concentration of 0.1 M or higher, such as 0.2 M or higher, or 0.5 M or higher, preferably 1.0 M or higher, or 1.5 M or higher, such as 1.8 M or higher. The compound according to Formula (II) may be included in the solution at a concentration of 10 M or less, such as 5.0 M or less, such as 4.0 M or less, preferably 3.0 M or less, or 2.5 M or less. The compound according to Formula (II) may be included in the solution at a concentration of from 0.1 to 10 M, such as from 0.2 to 5.0 M, or from 0.5 to 4.0 M, preferably from 1.0 to 3.0 M, or from 1.5 to 2.5 M.

Process

The claimed process for synthesising a compound according to Formula (I) requires subjecting a solution comprising a compound according to Formula (II) to a potential difference.

Without being bound by theory, it is thought that the potential difference causes an electrochemical reaction that transforms some of the compound according to Formula (II) into a molecule that can react with another molecule of the compound according to Formula (II). For example, where the compound according to Formula (II) has at least one X═O, a carbonyl group-containing molecule may be formed by application of the potential difference. In particular, where the compound according to Formula (II) is glycerol, acetone may be formed by the potential difference.

It has been observed by ion chromatography that formic acid is generated under the reaction conditions. It may be that the formic acid is generated by the electrochemical reduction of carbon dioxide. The formation of formic acid may be assisted by using an agent such as hydrogen peroxide. The formic acid may catalyse the reaction of the compound of Formula (I), such as glycerol, with a carbonyl group-containing molecule, such as acetone.

It may be that the concentration of carbonyl group-containing molecules in the solution before the potential difference is applied to the solution is very low, or that these are not present (i.e. the initial concentration). For example, the initial concentration of carbonyl group-containing molecules may be 0.1 M or lower, such as 0.01 M or lower, or 0.001 M or lower, such as 0.0001 M or lower. The concentration of carbonyl group-containing molecules may rise once the potential difference is applied. For example, the concentration of carbonyl group-containing molecules may be 0.0001 M or higher, or 0.001 M or higher, or 0.01 M or higher, or 0.1 M or higher after the potential difference has been applied, for example from 0.0001 M to 5 M, or from 0.001 M to 2 M.

It will be appreciated that the potential difference can be provided using a battery or power supply. In one embodiment the potential difference is provided from a renewable energy source, such as solar, wind or hydroelectric energy, or a stored form thereof, for example in a battery. This further reduces the carbon footprint of the process.

The skilled person will appreciate that the potential difference should be sufficiently high enough to perform the reaction. Thus, the potential difference may be 1.0V or higher, or 1.2V or higher, preferably 1.5V or higher, such as 1.7V or higher, or 1.9V or higher, for example 2.0V or higher. Too high a potential difference may lead to excessive oxidation of the solvent, such as water. Thus, the potential difference may be 5.0V or lower, or 4V or lower, such as 3.5V or lower, preferably 3.0V or lower, or 2.8V or lower, or 2.6V or lower, such as 2.5V or lower. The potential difference may be from 1.0V to 5.0V, or from 1.5V to 3.0V, such as from 2.0V to 2.5V.

The potential difference will cause an electrical current to flow through the solution. The current may be 0.1 mA or higher, such as 1.0 mA or higher, or 2.0 mA or higher, or 4.0 mA or higher. The current may be 10 A or lower, such as 1.0 A or lower, such as 800 mA or lower, or 500 mA or lower, such as 400 mA or lower, or 200 mA or lower. For example, the current may be from 0.1 mA to 1.0 A, or from 2.0 mA to 400 mA. It will be understood that the current may depend upon factors such as the size of the electrodes, the distance between the electrodes, and the contents (and concentration thereof) of the solution.

The potential difference may be applied for any suitable period of time as the compound of Formula (I) will begin to be synthesised almost immediately. For example, the potential difference may be applied for a time of 1 minute or longer, or 15 minutes or longer, such as 30 minutes or longer, or 1 hour or longer. The time may be 24 hours or less, such as 12 hours or less, or 6 hours or less, for example 4 hours or less or 3 hours or less. The time may be from 1 minute to 24 hours, such as from 30 minutes to 6 hours.

The process may include terminating the potential difference, i.e. ceasing the subjection of the solution to the potential difference, for example when the compound according to Formula (I) has formed or after a particular time period has elapsed.

The potential difference may be applied across two or more electrodes that are in contact with (e.g. submerged in) the solution. It will be understood that the electrodes should be electrically isolated from one another, other than via the solution. The electrodes may be made from any electrically conductive material. The skilled person will be aware of a variety of materials suitable for use as electrodes. For example, the electrodes may each be made of a material selected from the list consisting of graphite (e.g. coated graphite, such as $SnO_2$-coated graphite), glassy carbon (e.g. reticulated vitreous carbon), tin, cadmium, magnesium, stainless steel, zinc, copper, platinum, gold, rhodium, lead, copper, nickel (e.g. nickel foam or nickel mesh), palladium and/or silver. For example, the electrodes may each be made of a material selected from the list consisting of graphite, glassy carbon (e.g. reticulated vitreous carbon), magnesium, stainless steel, zinc, copper, platinum, gold, rhodium, lead, copper, nickel (e.g. nickel foam), palladium and/or silver. The electrodes may each be coated onto (i.e. supported on) a substrate such as ceramic, glass, alumina, plastic, or, preferably, graphite. The electrodes may each be gas diffusion electrodes. One or more plasma electrodes may be used. Plasma electrodes may be used independently of or in combination with one or more solid phase electrodes. Plasma electrodes are described by Bruggeman et al., 2016 *Plasma Sources Sci. Technol.* 25 053002 (DOI: 10.1088/0963-0252/25/5/053002). The electrodes may each be made of the same material or may be made of different materials.

Preferably at least one electrode (e.g. the anode) is made of a material selected from the list consisting of graphite, copper, copper-coated graphite, and zinc-coated graphite. Preferably at least one electrode (e.g. the anode) is made of a material selected from the list consisting of copper, copper-coated graphite, and zinc-coated graphite.

Preferably at least one electrode (e.g. the cathode) is made of a material selected from the list consisting of graphite and copper-coated graphite. More preferably one electrode (e.g. the anode) is copper and another electrode (e.g. the cathode) is graphite, or one electrode (e.g. the anode) is copper-coated graphite and another electrode (e.g. the cathode) is copper-coated graphite, or one electrode (e.g. the anode) is copper-coated graphite and another electrode (e.g. the cathode) is graphite, or one electrode (e.g. the anode) is zinc-coated graphite and another electrode (e.g. the cathode) is graphite. Preferably the anode is graphite. Preferably the anode and the cathode are graphite.

The process may include adding a carbonyl group-containing molecule, such as acetone, to the solution, or the process may require that the solution comprises a carbonyl group-containing molecule, before the potential difference is applied. The carbonyl group-containing molecule may not be a compound according to Formula (I) or (II).

The carbonyl group-containing molecule may be added (or contained) in an amount, relative to the compound of Formula (II), of 1 mol % or more, 2 mol % or more, 5 mol % or more, 10 mol % or more, or 20 mol % or more, or 50 mol % or more, or 75 mol % or more. The amount may be 1000 mol % or less, or 500 mol % or less, or 200 mol % or less, such as 150 mol % or less. For example, the carbonyl group-containing molecule may be added in an amount of 10 mol % to 1000 mol %, such as from 20 mol % to 500 mol %, or from 50 mol % to 200 mol %, or from 75 mol % to 150 mol % relative to the compound of Formula (II). It will be understood that an amount of 100 mol % would indicate that equimolar amounts of the carbonyl group-containing molecule and the compound of Formula (II) are present in the solution. The option to include a carbonyl group-containing molecule in the solution is most beneficial where both X groups in the compound of Formula (II) are not O, e.g. where one X group is O and the other X group is $NR^Y$, or where both X groups are $NR^Y$.

The carbonyl-group containing molecule may be a compound represented by Formula (III):

Formula (III)

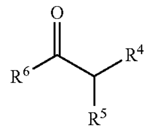

The options described above for the $R^4$ to $R^6$ groups of Formula (I) apply equally to the groups in Formula (III) with the same designation (e.g. $R^4$ of Formula (I) corresponds with $R^4$ of Formula (III)). In one embodiment the compound of Formula (III) has 40 carbon atoms or fewer, such as 30 carbon atoms or fewer, or 20 carbon atoms or fewer, preferably 15 carbon atoms or fewer, such as 10 carbon atoms or fewer, for example 7 carbon atoms or fewer, more preferably 5 carbon atoms or fewer. For example, the compound of Formula (III) may have from 2 to 40 carbon atoms, or from 2 to 20 carbon atoms, such as from 3 to 10 carbon atoms, or from 3 to 5 carbon atoms. For example, the carbonyl group-containing molecule may be acetone (CAS 67-64-1, propan-2-one). Acetone corresponds to Formula (III) wherein $R^4$ is hydrogen, $R^5$ is hydrogen, and $R^6$ is methyl.

The amount of the carbonyl group-containing molecule, such as the compound of Formula (III) (e.g. acetone), in the solution, relative to the total volume of the solution, may be 0.1 vol % or more, such as 0.5 vol % or more, preferably 1.0 vol % or more, such as 2.0 vol % or more, or 5.0 vol % or more, for example 8.0 vol % or more. The amount of the compound of Formula (III) (e.g. acetone) in the solution, relative to the total volume of the solution, may be 50 vol % or less, such as 40 vol % or less, or 30 vol % or less, preferably 20 vol % or less, such as 15 vol % or less, or 12 vol % or less. For instance, the amount may be from 0.1 to 50 vol %, or from 1.0 to 20 vol %.

However, while a carbonyl group-containing molecule, such as a compound of Formula (III), may be added to or comprised by the solution, most preferably the solution does not initially include such a molecule, and/or such a molecule is not added to the solution as this can be synthesised by the potential difference.

The solution (initially) comprises a compound according to Formula (II) in a solvent. The solution may comprise any suitable solvent, such as water, N,N-dimethylformamide, acetonitrile, tetrahydrofuran, dimethylsulfoxide, 1,2-dimethoxyethane, and/or dichloromethane. The solution is preferably an aqueous solution, i.e. it preferably contains water. The solution may include water in an amount of 30 vol % or more, such as 50 vol % or more, or 70 vol % or more, preferably 90 vol % or more, such as 95 vol % or more. The solvent may contain water in an amount of from 50 to 99 vol %, such as from 50 to 98 vol %, or from 50 to 95 vol %, such as from 70 to 90 vol %.

The solution may comprise an organic solvent, such as N,N-dimethylformamide, acetonitrile, tetrahydrofuran, dimethylsulfoxide, 1,2-dimethoxyethane, and/or dichloromethane, for example to increase the solubility of the compound of Formula (I) and/or the compound of Formula (II). The solution may contain organic solvent, such as those listed above, in an amount of 1 vol % or more, such as 5 vol % or more, or 10 vol % or more, for example 20 vol % or more, or 40 vol % or more. The amount of organic solvent may be 70 vol % or less, such as 50 vol % or less, or 30 vol % or less, such as 20 vol % or less, or 10 vol % or less. For example, the amount of organic solvent may be from 1 to 70 vol %, such from 5 to 50 vol %, or from 10 to 40 vol %.

The solution preferably comprises a Brønsted base, i.e. an alkali. Brønsted bases may include sulfate salts, dihydrogen phosphate salts, fluoride salts, nitride salts, acetate salts, hydrogen carbonate salts, hydrogen sulfate salts, ammonia, cyanide salts, carbonate salts, and hydroxide salts. A carbonate or hydrogen carbonate salt may be particularly preferable to supplement the solubilised carbon dioxide. The salts may be potassium, sodium, lithium, barium, magnesium, and/or calcium salts, preferably lithium, potassium and/or sodium salts, such as these salts of the above counterions. Particularly suitable bases include KOH, NaOH, LiOH, $Li_2CO_3$, $LiHCO_3$, $Na_2CO_3$, $NaHCO_3$, $K_2CO_3$, and $KHCO_3$. Preferably the base is KOH or $NaHCO_3$. More preferably KOH is used as a base.

The Brønsted base may be included in the solution at a concentration of 0.1 M or higher, such as 0.2 M or higher, or 0.5 M or higher, preferably 1.0 M or higher, or 1.5 M or higher, such as 1.8 M or higher. The Brønsted base may be included in the solution at a concentration of 10 M or less, such as 5.0 M or less, such as 4.0 M or less, preferably 3.0 M or less, or 2.5 M or less. The Brønsted base may be included in the solution at a concentration of from 0.1 to 10 M, such as from 0.2 to 5.0 M, or from 0.5 to 4.0 M, preferably from 1.0 to 3.0 M, or from 1.5 to 2.5 M. In one embodiment the solution contains a Brønsted base selected from the list consisting of KOH, NaOH, LiOH, $Na_2CO_3$, $NaHCO_3$, $K_2CO_3$, and $KHCO_3$ at a concentration of from 0.1 to 10 M, such as from 0.5 to 4.0 M.

The solution may contain an inorganic salt (e.g. the inorganic salt may be added to the solution, preferably before the application of the potential difference to the solution). Preferably the inorganic salt is a salt of a group 1 or group 2 metal, such as lithium, sodium, potassium, rubidium, beryllium, magnesium, calcium, strontium and/or barium. Preferably the inorganic salt is a salt of a group 1 metal, such as lithium, sodium, potassium, and/or rubidium. More preferably the inorganic salt is a salt of sodium and/or potassium. The inorganic salt may be a metal halide salt, such as a group 1 or group 2 metal halide salt. The halide may be fluoride, chloride, bromide or iodide, preferably fluoride, chloride or bromide, more preferably chloride.

The inorganic salt may be included in the solution at a concentration of 0.01 M or higher, such as 0.02 M or higher, or 0.05 M or higher, preferably 0.1 M or higher, or 0.2 M or higher, such as 0.4 M or higher. The inorganic salt may be included in the solution at a concentration of 10 M or lower, such as 5.0 M or lower, such as 2.0 M or lower, preferably 1.5 M or lower, or 1.0 M or lower, such as 0.8 M or lower. The inorganic salt may be included in the solution at a concentration of from 0.01 to 10 M, such as from 0.05 to 2.0 M, or from 0.1 to 1.0 M, preferably from 0.2 to 0.8 M. In one embodiment the solution contains a inorganic salt selected from the list consisting of a salt (e.g. halide) of a group 1 or group 2 metal, such as lithium, sodium, potassium, rubidium, beryllium, magnesium, calcium, strontium and/or barium at a concentration of from 0.01 to 10 M, such as from 0.2 to 0.8 M.

Preferably the solution comprises and/or is contacted with carbon dioxide. Without being bound by theory it is thought that the carbon dioxide dissolves to provide carbonate ions, which assist the process. This provides a use for this fossil fuel by-product.

Preferably the solution is substantially saturated (e.g. 90% saturated or more, or 95% saturated or more, or 99% saturated or more, by weight) with carbon dioxide prior to the solution being subjected to the potential difference. Carbon dioxide may be bubbled through the solution while it is being subjected to the potential difference. A stream of carbon dioxide may be passed through and/or over the solution. For example, the stream of carbon dioxide may include carbon dioxide at a concentration of 1 vol % or higher, such as 10 vol % or higher, or 50 vol % or higher, or 90 vol % or higher. It will be appreciated that the process does not require high pressures but that, nevertheless, high pressures may be used. The carbon dioxide may therefore be provided (e.g. whilst the potential difference is applied) at a pressure of 50 kPa or higher, preferably 80 kPa or higher, or 90 kPa or higher, such as 100 kPa or higher, or at a pressure of 5 MPa or less, such as 2 MPa or less, or 1 MPa or less, for example 500 kPa or less, or 300 kPa or less, preferably 200 kPa or less, such as 150 kPa or less, or 120 kPa or less. For example, the pressure may be from 50 kPa to 5 MPa, for example from 80 kPa to 1 MPa, for example from 90 kPa to 200 kPa.

Preferably the solution either is contacted with or contains $CO_2$, and also contains a Brønsted base.

The solution may be exposed to a flow or stream of carbon dioxide, for example by bubbling through the solution and/or during the application of the potential difference, in an amount of 0.01 SCCM (standard cubic centimetres per minute) per mL of reaction volume (i.e. SCCM/mL) or more, such as 0.05 SCCM/mL or more, preferably 0.1 SCCM/mL or more, or 0.5 SCCM/mL or more, for example 1 SCCM/mL or more, or 1.5 SCCM/mL or more. The amount may be 50 SCCM/mL or less, such as 20 SCCM/mL or less, preferably 10 SCCM/mL or less, for example 5 SCCM/mL or less, or 4 SCCM/mL or less, such as 3 SCCM/mL or less. The amount may be from 0.01 SCCM/mL to 50 SCCM/mL, such as from 0.1 SCCM/mL to 10 SCCM/mL.

As noted above, it has been observed that formic acid is generated under the reaction conditions, which may be generated by the electrochemical reduction of carbon dioxide.

The solution may comprise an oxidising agent, such as a peroxide, e.g. hydrogen peroxide. The oxidising agent, such as hydrogen peroxide, may facilitate the formation of an acidic agent such as formic acid from the carbon dioxide. Alternatively or additionally, the oxidising agent, such as hydrogen peroxide, may be reduced to provide a source of protons under the electrochemical conditions, which may catalyse the process (e.g. the condensation of the compound of Formula (I) with the compound of Formula (III)). The amount of oxidising agent, such as hydrogen peroxide, in the solution, relative to the total volume of the solution, may be 0.1 vol % or more, such as 0.5 vol % or more, preferably 1.0 vol % or more, such as 2.0 vol % or more, or 3.0 vol % or more, for example 4.0 vol % or more. The amount of the oxidising agent (e.g. hydrogen peroxide) in the solution, relative to the total volume of the solution, may be 50 vol % or less, such as 40 vol % or less, or 30 vol % or less, preferably 20 vol % or less, such as 15 vol % or less, or 12 vol % or less, e.g. 10 vol % or less, such as 8 vol % or less, or 5 vol % or less. For instance, the amount may be from 0.1 to 50 vol %, or from 1.0 to 20 vol %. The skilled person will be aware of other means to provide an acidic agent (such as formic acid) or protons to the solution, which may be used as an alternative to oxidising agents such as hydrogen peroxide.

As an alternative to or in addition to the carbon dioxide and/or the oxidising agent, the solution may contain an acidic agent (i.e. Brønsted acid), or the conjugate base thereof. The acidic agent may be an inorganic acid, such as those selected from the list consisting of hydrochloric acid, hydrobromic acid, hydroiodic acid, nitric acid, sulfuric acid and phosphoric acid. The acidic agent preferably is an organic acid, such as an organic compound containing a carboxylic acid, sulphate, and/or phosphate group. Carboxylic acid groups are preferable. More preferably the organic acid is selected from the list consisting of carbonic acid, citric acid, lactic acid, maleic acid, formic acid, acetic acid, propionic acid, butyric acid, valeric acid, caprylic acid, oxalic acid, malic acid and benzoic acid. More preferably the organic acid is formic acid, acetic acid or propionic acid. Most preferably the organic acid is formic acid. It will be understood that conjugate bases of these inorganic and organic acids are included within the disclosure and may alternatively or additionally be added to or contained by the solution. Acidic agents are known to catalyse the formation of ketals from a compound containing a diol and a compound containing a carbonyl group, and this may be the role that the acidic agent, e.g. formic acid, takes in the process, for example once the carbonyl compound has been electrochemically generated. Conjugate bases of the acidic agents may include the sodium, potassium, lithium, and/or ammonium salts thereof.

The acidic agent or conjugate base thereof may be added or contained by the solution in an amount, relative to the compound of Formula (I), of 0.0001 mol % or more, or 0.001 mol % or more, such as 0.01 mol % or more, or 0.1 mol % or more, for example 1 mol % or more. The amount may be 50 mol % or less, such as 20 mol % or less, or 10 mol % or less, such as 2 mol % or less. The amount may be from 0.0001 mol % to 50 mol %, for example from 0.01 mol % to 10 mol %.

It will be appreciated that a carbonyl-group containing molecule, such as that of Formula (III), and a compound of Formula (I), which contains a diol, can condense under a conventional chemical reaction, i.e. without requiring the application of a potential difference. Thus, in a later stage of the reaction, perhaps once the acidic agent such as formic acid has been generated, the reaction mixture may be left or stirred, for a period of time. The yield of the compound of Formula (II) may increase during this period of time. For example, the period of time may be 30 seconds or more, or 2 minutes or more, such as 5 minutes or more, or 10 minutes or more. The period of time may be 7 days or less, or 2 days or less, or 1 day or less, such as 12 hours or less, or 6 hours or less, or 2 hours or less. The period of time may be from 30 seconds to 7 days, such as from 2 minutes to 12 hours.

It will be appreciated that the process does not require high pressures but that, nevertheless, high pressures may be used. The pressure (of the solution), whilst the potential difference is applied, may be 50 kPa or higher, preferably 80 kPa or higher, or 90 kPa or higher, such as 100 kPa or higher, or of 5 MPa or less, such as 2 MPa or less, or 1 MPa or less, for example 500 kPa or less, or 300 kPa or less, preferably 200 kPa or less, such as 150 kPa or less, or 120 kPa or less. For example, the pressure may be from 50 kPa to 5 MPa, for example from 80 kPa to 1 MPa, for example from 90 kPa to 200 kPa.

It will be appreciated that the process does not require high temperatures but that, nevertheless, high temperatures may be used. The solution may be at a temperature of 100° C. or less whilst the potential difference is applied, such as 90° C. or lower, or 80° C. or lower, preferably 50° C. or lower, or 40° C. or lower, for example 30° C. or lower. The solution may be at a temperature of 0° C. or higher whilst the potential difference is applied, such as 10° C. or higher, or 15° C. or higher, such as 20° C. or higher. For example, the temperature of the solution whilst the potential difference is applied may be from 0° C. to 100° C., such as from 10° C. to 50° C., or from 15° C. to 40° C.

The process may include isolating the product, for example by extraction (e.g. liquid/liquid extraction), filtration and/or distillation. For example, the product may be isolated from the base or other inorganic materials by liquid/liquid extraction, distillation and/or filtration, or from excess glycerol or water by liquid/liquid extraction and/or distillation.

Reactor

The process can be performed in one or more reactors, or modules thereof.

A batch reactor may be used to perform the process. Examples of batch reactors include test tubes, round bottomed flasks and large scale (e.g. 100 L or more) reaction vessels.

FIG. 1 of the accompanying drawings shows an example of a batch reactor that can be used to perform the process of the present invention. This shows a carbon dioxide-saturated aqueous solution of glycerol and KOH 10, a magnetic stir bar (flea) 20 used to stir the reaction mixture, a copper-coated graphite electrode 30, and an uncoated graphite electrode 40, which is preferably a renewable energy power source.

However, it is preferred that the process is performed in a flow reactor.

FIG. 2 of the accompanying drawings illustrates a suitable exemplary flow reactor. The flow reactor includes power source 50 and conduit 60, shown in cross-sectional view, through which the carbon dioxide-saturated aqueous solution of glycerol and KOH 10 can flow, in order to prepare a continuous stream of the desired product, solketal. The conduit 60 is flanked by electrodes 30, 40, which the solution comes into contact with, and across which the potential difference is applied by power source 50, which is preferably a renewable power source.

The dimensions of a unit containing the conduit of a flow reactor may suitably be 6 cm×10 cm×2 cm, which could allow for a solution inlet flow rate of approximately 5 $cm^3/s$.

The skilled person will understand that flow reactors perform chemical reactions within conduits, the reaction mixture being a continuously flowing stream. Flow reactors can provide benefits in terms of heat transfer, increased mixing, increased safety, facile scaling up (through simple stacking of reactors in parallel), and facile automation. The flow reactor may be modular.

A suitable reactor, for example a flow synthesis reactor, to perform the process may be produced using three-dimensional printing, injection moulding and/or CNC milling. For example, three-dimensional printing may be used to prepare a reactor made of polymethylmethacrylate (PMMA).

Applications

It will be appreciated that the compounds of Formula (I) obtainable by the process of the first aspect, as defined by the second aspect, and the compositions of the third aspect will find application in a variety of fields, and can be incorporated into a variety of products. The compound of Formula (I) may be part of a composition. For example, the compounds of Formula (I) may be contained in a product that is:

a) a solvent;

b) a fuel, for example a liquid petroleum fuel, such as gasoline (petrol), diesel and/or kerosene;

c) a pharmaceutical intermediate;

d) an air care product, for example a fragrance diluent, base or carrier, such as for an air freshener (e.g. a plug-in air freshener, a diffuser, or a spray) or a candle;

e) a paint or varnish, such as an epoxy resin, for example for application to automobiles, metal and/or wood;

f) an ink, such as a printing ink;

g) a cleaning agent, such as a household or institutional cleaning agent, for example a surface cleaning agent and/or a degreaser; and/or h) a leather treatment agent, for example a penetrating agent, an adhesion promoter, a dye diluter, and/or a lacquer for paint.

It will be understood that the compounds of Formula (I) may be used in such products.

The compound of Formula (I) may be present in the product in an amount of 1 wt % or more, such as 5 wt % or more, or 10 wt % or more, for example 20 wt % or more, or 50 wt % or more. The amount may be from 1 wt % to 100 wt %, such as from 2 wt % to 99 wt %, or from 5 wt % to 95 wt %, for example from 10 wt % to 90 wt %, or from 20 wt % to 80 wt %.

DESCRIPTION OF THE DRAWINGS

Embodiments of the present invention will now be described by way of example with reference to the accompanying drawings, in which.

EXAMPLES

Preparation of Coated Graphite Electrodes

A saturated aqueous solution of $CuCl_2$ (10 mL) was prepared. A potential difference of 10 V was passed for 10 min across two graphite electrodes with fixed poles using an IKA ElectraSyn 2.0 cell. The resulting copper-coated electrode was dried at 110° C. overnight.

Other metal-coated electrodes can be prepared by the above method, exchanging the $CuCl_2$ for the desired metal halide salt. For example, $ZnCl_2$ can be used to prepare zinc-coated graphite electrodes.

Synthesis of Solketal

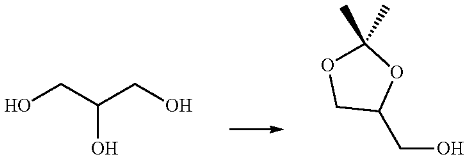

Glycerol Solketal

Figure 1:
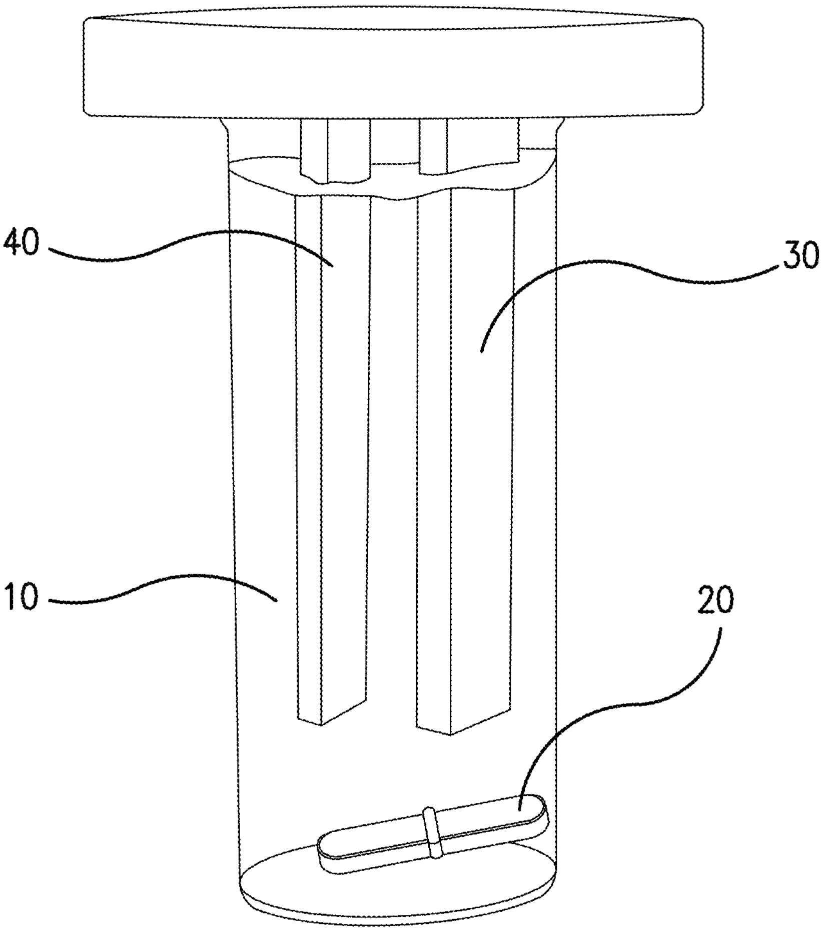
FIG. 1 shows a batch reactor that can be used to perform the process of the present invention.
Figure 2:
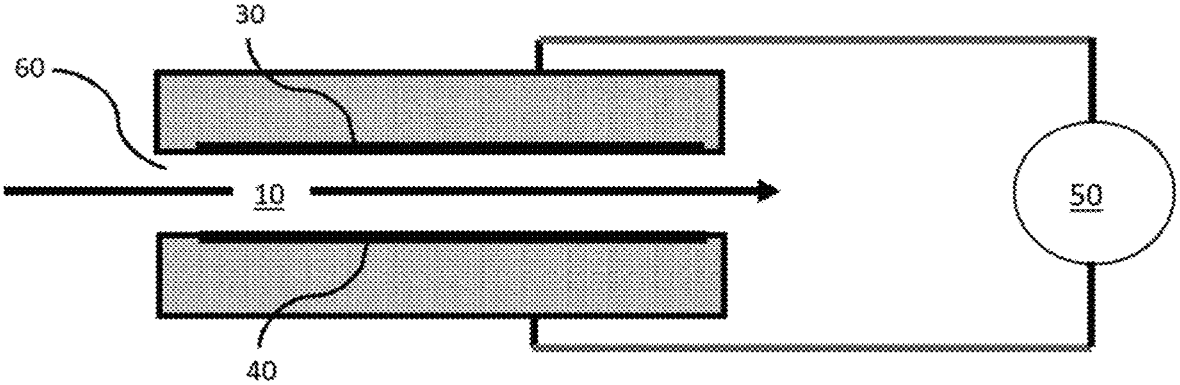
FIG. 2 illustrates a suitable exemplary flow reactor.

First Protocol:

Prior to the reaction, all equipment was new and dried to make sure that no trace of acetone was present. A mixture of glycerol (2 M, 2.5 mL) and KOH (2 M, 2.5 mL) was prepared and a constant stream of carbon dioxide was bubbled through the resulting solution at 1 atm pressure for 30 minutes to saturate the solution with carbon dioxide prior to the reaction taking place. The apparatus used for this experiment is shown in FIG. 1.

Whilst continuing the stream of carbon dioxide through the solution, the solution was electrolysed at room temperature using a potential difference of 2 V for 2 hours using an IKA ElectraSyn 2.0 cell. Water was subsequently removed under reduced pressure and the residue obtained was analysed by gas chromatography-mass spectrometry, nuclear magnetic resonance spectroscopy and infra-red spectroscopy to confirm the presence of solketal. The yield of solketal was calculated by GC-MS, by comparison to a calibration curve.

Figure 3:
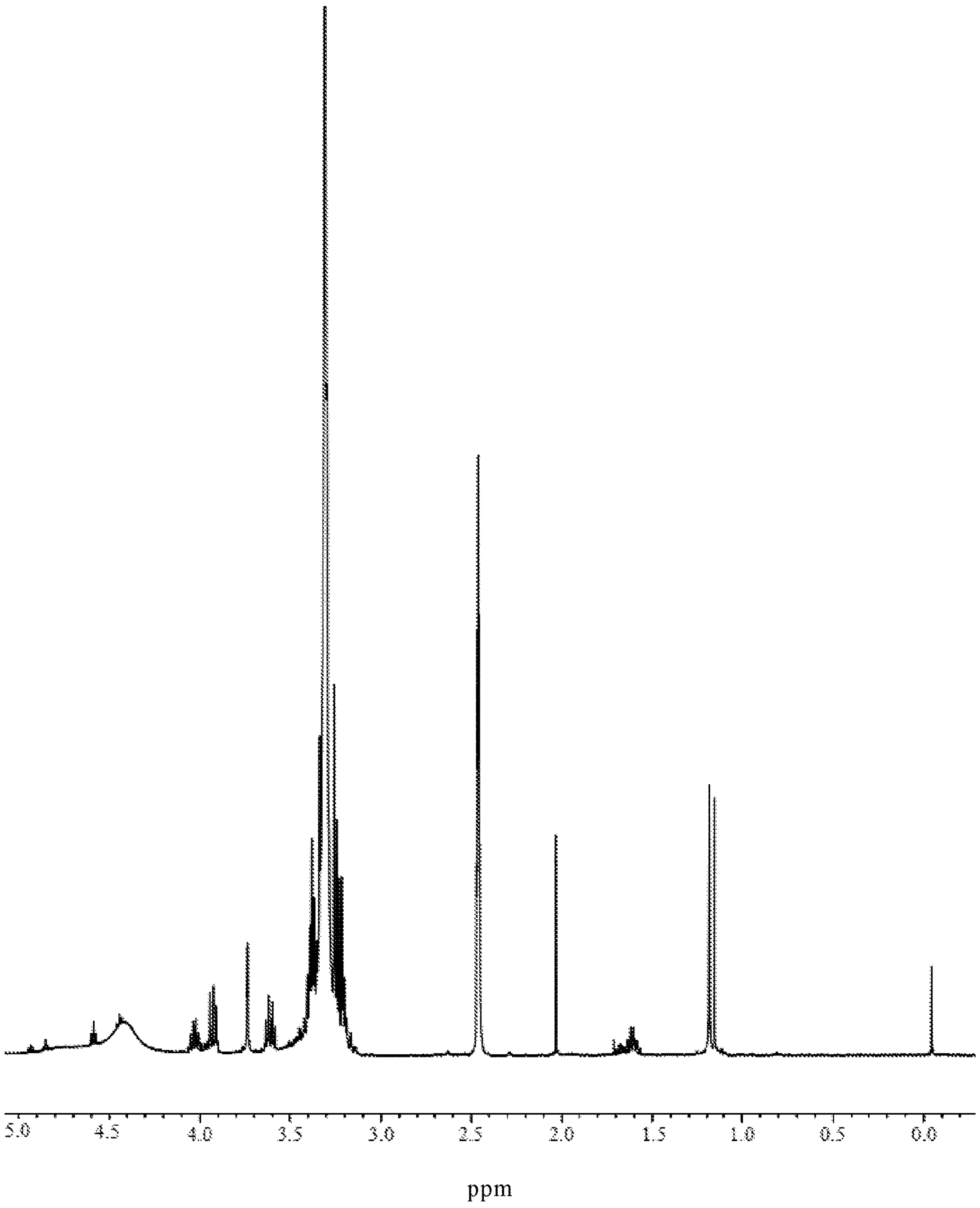
FIG. 3 shows the $^1$H NMR spectrum of the reaction product, which correlates with literature data for solketal.
Figure 4A:
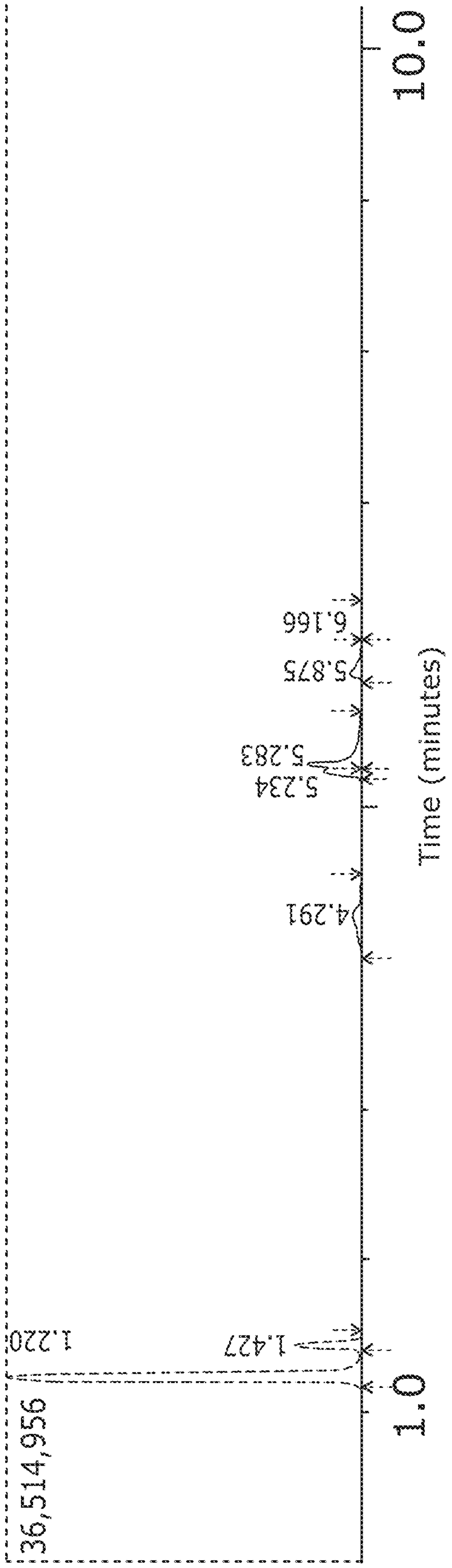
FIG. 4*a* shows the GC-MS chromatogram for the reaction product.
Figure 4B:
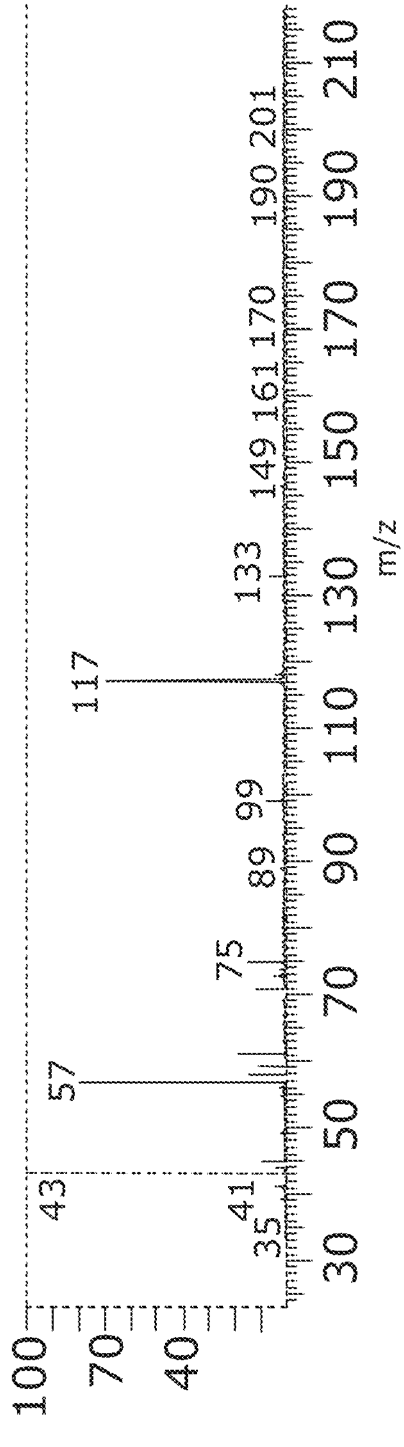
FIG. 4*b* shows the mass spectrum of the peak at 5.283 minutes in the chromatogram of FIG. 4*a*.

FIG. 3 shows the $^1$H NMR spectrum of the reaction product of the first protocol, which correlates with literature data for solketal. FIG. 4*a* shows the GC-MS chromatogram for the reaction product and FIG. 4*b* shows the mass spectrum of the peak at 5.283 minutes in the chromatogram of FIG. 4*a*, which shows solketal, with a $M+H^+$ m/z of 133.

The electrodes used and yields obtained in the experiments are shown in Table 1, below.

TABLE 1

| Electrodes Anode/Cathode | Formic acid yield (%) | Solketal yield (%) | Current (mA) |
|---|---|---|---|
| Cu/graphite | 0.001 | 63.04 | 5-6 |
| Cu-coated graphite/Cu-coated graphite | 0 | 56.35 | 70-100 |
| Cu-coated graphite/graphite | 0.2 | 63.13 | 70-100 |
| Zn-coated graphite/graphite | 0.05 | 68.11 | 5-6 |

Solketal was successfully produced in calculated yields of from 56 to 68%. The amounts of the by-product, formic acid, that were produced were very low.

Second Protocol:

A solution (10 mL) containing glycerol (2 M), KOH (2 M) acetone (1 mL) was prepared. The solution was subjected to a potential difference of 2 V using an ElectraSyn 2.0 cell for 2 h using a carbon anode and a copper cathode, whilst being supplied with 20 SCCM of $CO_2$. The resultant solution was collected in a GC vial and diluted (500 μL sample+200 μL 2-propanol+50 μL internal standard) and was analysed by GC equipped with a Stabilwax column. The yield of solketal was calculated by GC-MS, by comparison to a calibration curve.

Third (i.e. Two Stage) Protocol:

An aqueous solution of $H_2O_2$ (500 μL) and NaCl (35 ppm/0.35 g) in water (total volume 10 mL) was prepared. The solution was subjected to a potential difference of 2 V using an ElectraSyn 2.0 cell, using a carbon anode and a copper cathode, whilst being supplied with $CO_2$ (20 SCCM). After 1 hour, glycerol (1 M) and acetone (1.0 mL) was added. After a further 1 hour, the reaction mixture was collected in a GC vial (500 μL sample+200 μL 2-propanol+50 μL internal standard) and was analysed by GC equipped with a Stabilwax column. The yield of solketal was calculated by GC-MS, by comparison to a calibration curve.

Following this protocol solketal (20% yield) was obtained.

GC-MS analysis of the reaction mixture revealed that a compound having the molecular formula $C_7H_{12}O_2$, which could have been ethyl cyclopentanolone, was generated as a by-product of the reaction. This was surprising and was postulated as perhaps being characteristic of the process of the first aspect as opposed to conventional condensation reaction being used to prepare solketal.

Comparative Experiment Without Potential Difference

In a comparative experiment performed under the first protocol as detailed above but with no potential difference applied across the electrodes, no reaction occurred.

CONCLUSIONS

- Solketal was produced without any acids, let alone strong acids, or heterogeneous catalysts being added to the reaction mixture, as would be required by conventional processes for producing solketal.
- Solketal was produced at room temperature, rather than at the high temperatures that would be required by conventional processes for producing solketal.
- Solketal was produced at standard atmospheric pressure, rather than at the high pressures that would be required by conventional processes for producing solketal.
- Solketal was produced without requiring acetone to be added or requiring excess acetone to be removed by distillation to isolate solketal, unlike the conventional processes for producing solketal. The use of new, dry equipment ensured that acetone was not present before the potential difference was applied to the solution.

This reaction requires a potential difference to be applied.

Therefore, the process of the present invention has a number of distinct advantages over conventional processes for producing compounds of Formula (I), such as solketal.

The invention claimed is:

1. A process for synthesising a compound according to Formula (I):

Formula (I)

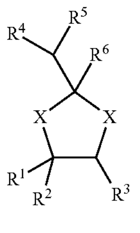

wherein the process comprises:

subjecting a solution comprising a compound according to Formula (II):

Formula (II)

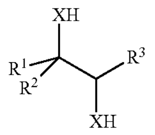

to a potential difference, wherein, for the compounds according to Formulae (I) and (II):

each X is independently selected from the group consisting of O, S, $NR^Y$ and $PR^Y$, each of $R^1$ to $R^6$ and $R^Y$ is selected from the group consisting of hydrogen, $C_1$-$C_{12}$ alkyl, $C_2$-$C_{12}$ alkenyl, $C_2$-$C_{12}$ alkynyl, $C_6$-$C_{12}$ aryl, and $C_3$-$C_{12}$ heterocyclyl, each of $R^1$ to $R^6$ and $R^Y$ optionally contains one or more heteroatom containing groups, and wherein Formulae (I) and (II) include tautomeric and stereochemically isomeric forms thereof, wherein the potential difference is applied across two or more electrodes that are in contact with the solution, wherein the two or more electrodes comprise a first electrode and a second electrode, and wherein either:

a) the first electrode is made of copper and the second electrode is made of graphite, or b) the first electrode is made of copper-coated graphite and the second electrode is made of copper-coated graphite, or c) the first electrode is made of copper-coated graphite and the second electrode is made of graphite, or d) the first electrode is made of zinc-coated graphite and the second electrode is made of graphite.

2. The process of claim 1, wherein the solution further comprises a Brønsted base.

3. The process of claim 2, wherein the Brønsted base is selected from the group consisting of KOH, NaOH, LiOH, $Li_2CO_3$, $LiHCO_3$, $Na_2CO_3$, $NaHCO_3$, $K_2CO_3$, and $KHCO_3$.

4. The process of claim 1, wherein the solution further comprises and/or is contacted with carbon dioxide.

5. The process of claim 1, wherein the solution is under a pressure whilst the potential difference is applied, and wherein the pressure is 5 MPa or less.

6. The process of claim 1, wherein the first electrode is an anode and the second electrode is a cathode.

7. The process of claim 1, wherein each of $R^1$ to $R^6$ and $R^Y$ is selected from the group consisting of hydrogen, $C_1$-$C_8$ alkyl, $C_2$-$C_8$ alkenyl, $C_2$-$C_8$ alkynyl, $C_6$-$C_8$ aryl, and $C_4$-$C_8$ heterocyclyl.

8. The process of claim 7, wherein the compound according to Formula (I) is solketal:

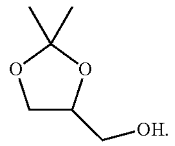

9. The process of claim 7, wherein the compound according to Formula (II) is glycerol:

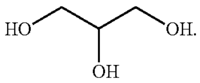

10. The process of claim 1, wherein X is O.

11. The process of claim 1, wherein the one or more heteroatom containing groups is an alcohol.

12. The process of claim 1, wherein the process further comprises, after subjecting the solution comprising the compound according to Formula (II) to the potential difference, isolating the compound according to Formula (I).

13. The process of claim 1, wherein the solution further comprises a carbonyl group-containing molecule.

* * * * *